(12) United States Patent
Chuang et al.

(10) Patent No.: US 8,876,735 B2
(45) Date of Patent: Nov. 4, 2014

(54) APPARATUS AND METHODS FOR IDENTIFYING A TISSUE INSIDE A LIVING BODY

(75) Inventors: Cheng-Hsin Chuang, Tainan (TW); Yi-Rong Liou, Tainan (TW)

(73) Assignee: Southern Taiwan University, Tainan (TW)

( * ) Notice: Subject to any disclaimer, the term of this patent is extended or adjusted under 35 U.S.C. 154(b) by 832 days.

(21) Appl. No.: 13/116,092

(22) Filed: May 26, 2011

(65) Prior Publication Data
US 2012/0302922 A1  Nov. 29, 2012

(51) Int. Cl.
A61B 5/00 (2006.01)
(52) U.S. Cl.
USPC .......................................................... 600/587
(58) Field of Classification Search
USPC .......... 600/550, 552, 553, 557, 587; 606/170, 606/174
See application file for complete search history.

(56) References Cited

U.S. PATENT DOCUMENTS

| | | | | |
|---|---|---|---|---|
| 3,008,239 A | * | 11/1961 | Lange | 33/558.04 |
| 4,159,640 A | * | 7/1979 | Leveque et al. | 73/81 |
| 4,503,865 A | * | 3/1985 | Shishido | 600/587 |
| 5,766,137 A | * | 6/1998 | Omata | 600/587 |
| 6,351,549 B1 | * | 2/2002 | Souluer | 382/131 |
| 7,311,676 B2 | * | 12/2007 | Park | 600/587 |
| 7,955,278 B1 | * | 6/2011 | Sarvazyan | 600/587 |
| 8,317,726 B2 | * | 11/2012 | Timberlake et al. | 600/564 |
| 8,328,730 B2 | * | 12/2012 | Sakagami et al. | 600/557 |
| 8,529,599 B2 | * | 9/2013 | Holsten | 606/219 |
| 8,721,565 B2 | * | 5/2014 | Hashimshony et al. | 600/587 |

OTHER PUBLICATIONS

Office Action—Taiwanese Patent Office, Jul. 29, 2013.
A. Atieh, et al, a Piezoresistive Based Tactile Sensor for Use in Minimally Invasive Surgery, 37th Annual Northeast Bioengineering Conference. Apr. 1-3, 2011, Montreal, Quebec, Canada.
Qasaimeh et al, An Endoscopic Grasper With Corrugated Plate-Shaped Tactile Sensors, Journal of Mechanics of Materials and Structures, vol. 4, No. 5, Mathematical Sciences Publishers, pp. 913-926. May 2009, vol. 4.
Wen-Pin LO, Flexible Piezoelectric Tactile Sensor With Structural Electrodes Array, Department of Mechanic Engineering, Southern Taiwan University of Science and Technology, Jul. 23, 1996.

* cited by examiner

*Primary Examiner* — Max Hindenburg
(74) *Attorney, Agent, or Firm* — Gottlieb, Rackman & Reisman, P.C.

(57) ABSTRACT

The present invention provides an apparatus for performing a measurement inside a living body. The apparatus includes a first sensing element, a manipulating device and an analyzing device. The first sensing element performs the measurement. The manipulating device is coupled to the first sensing element, and manipulates the first sensing element. The analyzing device is for analyzing the measurement.

17 Claims, 9 Drawing Sheets

APPARATUS AND METHODS FOR IDENTIFYING A TISSUE INSIDE A LIVING BODY

FIELD OF THE INVENTION

The present invention relates to measurement for a material property, particularly an apparatus as well as the method thereof for measuring a material property of a tissue inside a living body.

BACKGROUND OF THE INVENTION

The question whether a tissue inside a living body is normal is often faced by medical or biotechnical personnel. The number of people who suffer malignant tumors has been rising year by year, and the mortality rate due to cancer has been second only to cardiovascular diseases. Therefore, it is an important issue of diagnosis and treatment for cancers at the early stage thereof. In recent years, the development of endoscopes has been matured. Both dimensions and functions of endoscopes are improved, so endoscopes are increasingly popular for the use of diagnosis of diseases inside human bodies. Nevertheless, the current examination with endoscopes can only provide image information of the surface of the tissues, which is of limit use for the need of diagnosis of tumors at the early stages, and therefore tissue slices are usually necessary for the need of pathology judgment. However, there exist of risk of massive hemorrhages during the operation for obtaining tissue slices. If an endoscope is equipped with the function being capable of identifying characters related to hardness of a tissue, and the result thereof can be of good use for determining whether the inspected tissue is in normal condition, it will be beneficial to the diagnosis of tumors in the early stages while the mentioned risk due to slicing the tissue can be avoided. Similarly, the method of for measuring a material property of a tissue inside a living body can be adopted for observing whether there has been a change, either in terms of quality or in terms of material property, of an embedded material (such as the filling material commonly used for plastic surgeries) inside a living body, or it can also be used for observing the development of connective tissues inside human body after surgery restoration.

It would be an advanced function of a tactile sensor for being able to verify either the softness or the hardness of a matter, particularly being utilized to identify different portions of an animal's body based on the softness or hardness thereof. However, those tactile sensing apparatuses known to the art are either too complicated or short in performance. These shortages render the currently prevailed tactile sensors hard to be used for identifying physical materials as soft as tissues of human bodies.

Please refer to FIG. 1, which is a schematic diagram illustrating an endoscope 10 capable of verifying the hardness of a tissue. It can be observed from FIG. 1 that, an external structure 12 is disposed at the front end of a traditional endoscope 11 for adapting a spring 13 with an observation window 14 and a filter 15 at the front. The axis of the endoscope 10 lies along the direction of the Z-axis. FIG. 2 shows a cross-sectional view of the spring 13 of the endoscope 10 at a plan A-A illustrated in FIG. 1. Apparently, the endoscope 10 is good for used in analyzing material properties, such as hardness or elastic coefficient, of a matter or a tissue in front of the endoscope 10, by collecting the deformation of the spring 13 due to a force Fz along the direction of Z-axis. However, according to FIG. 2, those external forces at either the direction of X-axis Fx and the direction of Y-axis Fy is not measurable by the endoscope 10. Besides, the effectiveness in terms of determining the degree of hardness for the apparatus illustrated in FIG. 1 is limited, and sometimes causes misjudging.

Some people suggested a method for verifying the mechanical properties of a matter by using the transmission of vibration signals. According to a research resulting with low-frequency vibrations, however, the measurement at low power may easily be disturbed by noises, and the accuracy thereof is insufficient. Some other sensing device for detecting material properties based on different physical concepts are also hard to be used for distinguishing soft materials such as sponge and gelatin.

According to the above-mentioned, there is a need to develop a new method for measuring a material property of a tissue inside a living body to overcome all those deficiencies of the prior arts.

SUMMARY OF THE INVENTION

It is an objective of the present invention provide a method and apparatus to instantly verify the material property of a tissue inside a living body. To achieve the abovementioned objective, the present invention provides an apparatus for performing a measurement inside a living body. The apparatus includes a first sensing element, a manipulating device and an analyzing device. The first sensing element performs the measurement. The manipulating device is coupled to the first sensing element, and manipulates the first sensing element. The analyzing device is for analyzing the measurement.

In accordance with another aspect of the present invention, a sensing apparatus used inside a living body is provided. The sensing apparatus includes a first tactile sensing element and a manipulating device which manipulates the first tactile sensing element.

In accordance with a further aspect of the present invention, a method of measuring a tissue of a living body is provided. The method comprises steps of: (a) providing a pair of working elements pivotally connected; (b) measuring a parameter of the tissue of the living body by using the pair of working elements; and (c) analyzing the parameter.

The above objects and advantages of the present invention will be more readily apparent to those ordinarily skilled in the art after reading the details set forth in the descriptions and drawings that follow, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

If a body includes two portions which are obviously distinguishable in terms of a mechanical property and disposed at right and left, stresses measured from the two portions will be different when a compression is loaded to the body from top to its bottom, for the harder portion of the body bears more loading. The difference of the stresses measured from the two portions varies due to the mechanical property of the material that provides the compression.

Figure 1:
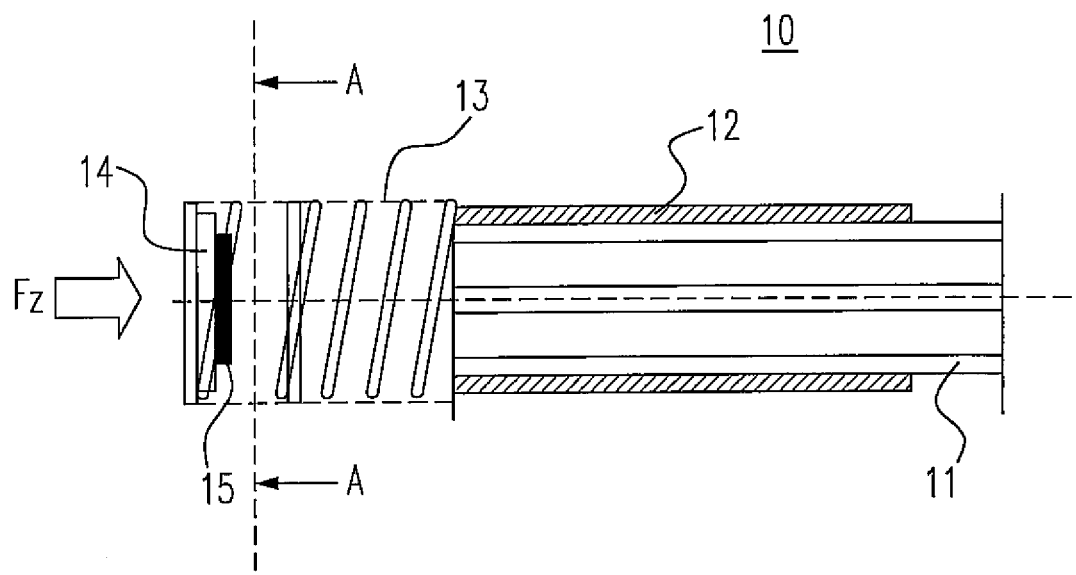
FIG. 1 is a schematic diagram showing an endoscope according to the prior art.
Figure 2:
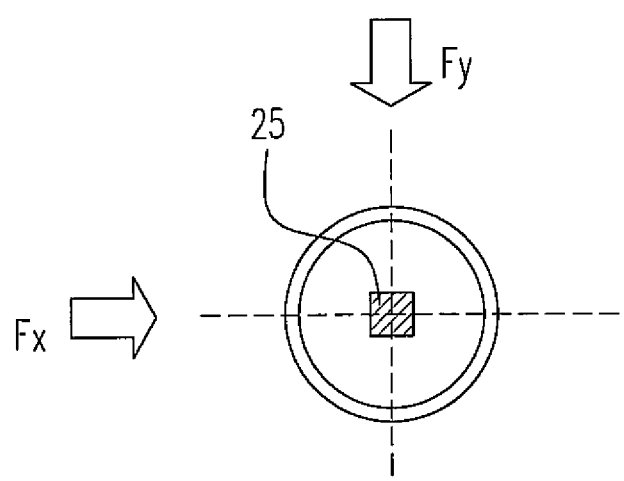
FIG. 2 is a schematic diagram showing a cross-sectional view of the spring 13 of the endoscope 10 at a plan A-A illustrated in FIG. 1.
Figure 3A:
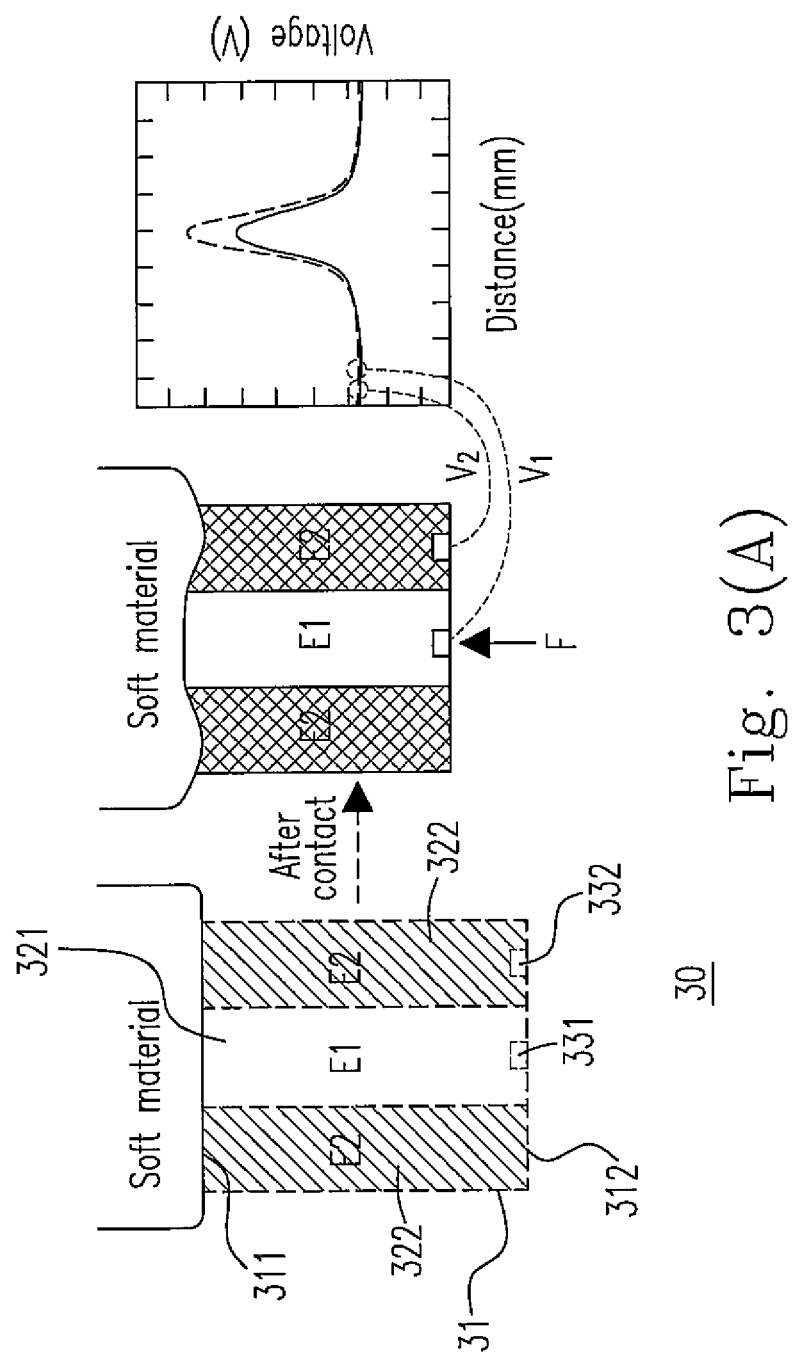
FIGS. 3(A) and 3(B) are schematic diagrams showing the method for measuring a material property of a body under inspection in accordance with one embodiment of the present invention.

Please refer to FIG. 3(A), which is a schematic diagram showing an apparatus and a method thereof for measuring a material property of a body under inspection in accordance with one embodiment of the present invention. According to FIG. 3(A), a measurement material 30 with a first surface 311 and a second surface 312 is composed of a first portion 321 and a second portion 322, where the mechanical property of the materials (for example an elastic coefficient) of the first and the second portions 321, 322 are E1 and E2 respectively, and there is a significant difference between E1 and E2. A first and a second locations 331, 332 are marked on the second surface 312, and face the first and the second portions 321, 322 respectively, for the need of further descriptions set forth below. It can be observed from the illustration of FIG. 3(A) that, the second surface 321 of the measurement material 30 comprises surfaces of the first portion 321 and the second portion 322 separately. To describe in a convenient way, the first and the second portions 321, 322 are disposed along a horizontal direction, while the first and the second surfaces 311, 312 are the upper and the bottom surfaces of the measurement material 30 respectively, and the value of the elastic coefficient E1 is larger than that of E2.

Notably, the disposition of embodiment for achieving the anticipated effects of the present invention is not limited to the above-mentioned example. Elastic coefficients indicate the degree of softness or hardness. As for the same type of material, the density thereof is also related to the elastic coefficients or hardness thereof. Therefore, the present invention is applicable for estimating material properties of a specimen based on the differences in terms of hardness or density of the two portions of the measurement material.

Referring to FIG. 3(A), a soft specimen is placed on the first surface 311 of the measurement material 30, external forces F are applied to compress both the soft specimen and the measurement material 30 simultaneously, and deformations result in the contact due to the compression occur at the areas near the first surface 311. According to the illustration, it can be observed that the deformation of the second portions 322 is larger than that of the first portion 321, for the first portion 321 has a larger elastic coefficient (Young's Modulus for example) E1 which indicates a relatively tougher material property. At this moment, one may obtain different stress values by measuring the first and second locations 331, 332, based on the above-mentioned concept of Mechanics of Materials. According to one preferred embodiment of the present invention, a simple method is to dispose a pressure-sensing material (e.g. piezoelectric material, not shown) underneath the second surface 312 to collect voltage values V1, V2 from locations near the first and second locations 331, 332 respectively. Usually the voltages produced from a piezoelectric material of a uniform thickness are positively propositional to the pressure stresses at the measurement areas. Thus, the ratio of the two stresses measured at the locations 331, 332 can be obtained from that of the two voltages V1, V2.

The right portion of FIG. 3(A) illustrates the values of the voltages V1, V2 measured from different locations underneath the first and second portions 331, 332, where the dotted line indicate the values of V1, the solid lines indicate the values of V2, and the distance between the two different locations corresponding to each pair of data is shown on the X-axis. The experimental results are in consistence with the expectation of the above-mentioned concept, which anticipates the values of V1 shall always above the values of V2.

Figure 3B:
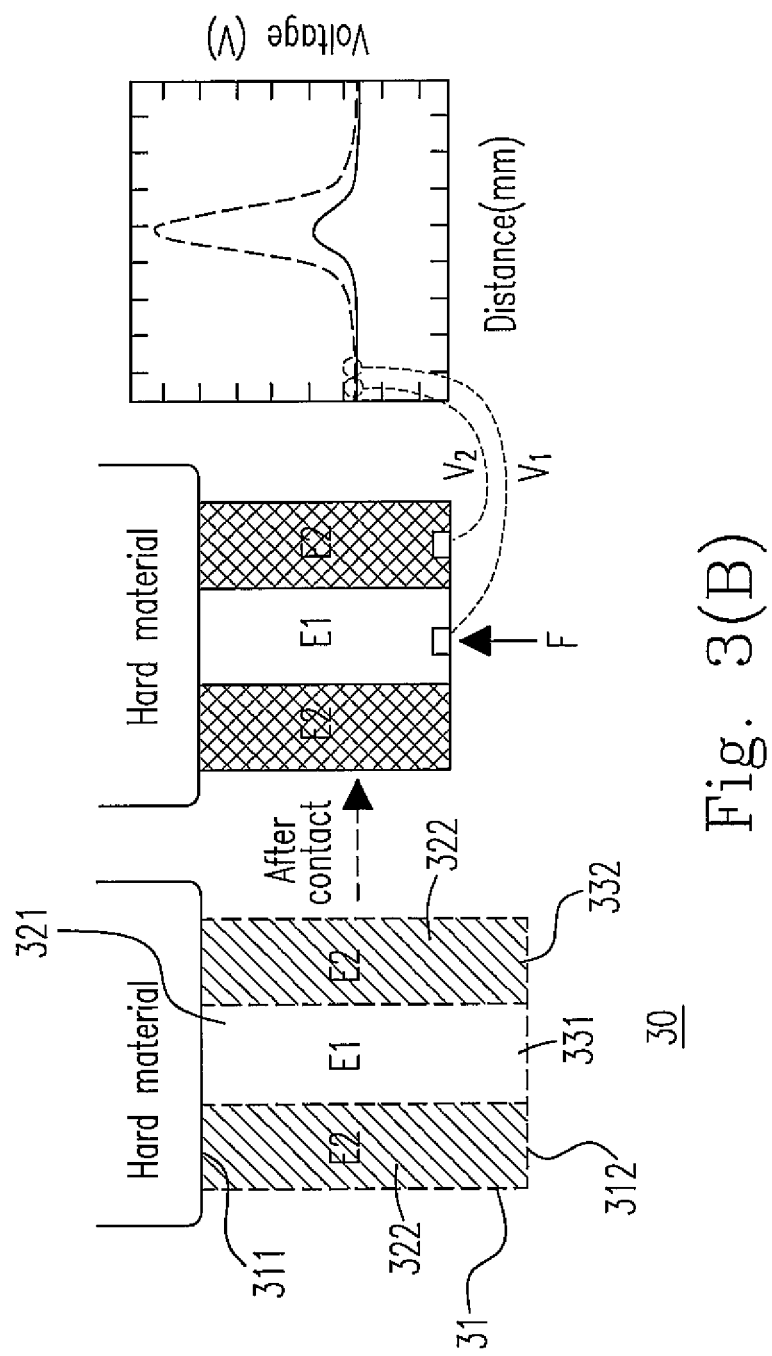

Please refer to FIG. 3(B), which illustrates the same measurement material 30 for measuring a specimen of a harder material. According to the illustrations, external forces F are applied to compress both the hard specimen and the measurement material 30 simultaneously. However, deformations result in the contact due to the compression occur at the areas near the first surface 311 are much less that those in the illustrations of FIG. 3(A). It can be observed that the voltage difference between V1 and V2 resulting from the some device allocation with that in FIG. 3(A), except the material property of the specimen, is significantly higher in FIG. 3(B) (referring to the right portion of FIG. 3(B)). Comparing the differences between those illustrations in FIGS. 3(A) and 3(B), one may obtain the ratios of V1 to V2 or the corresponding stress ratios, which can be used for estimating material properties relevant to the softness or hardness of the tested material, for examples, hardness or elastic coefficients. When the ratio of V1 to V2 is higher, it can be realized that the Young's modulus of the material of the tested matter is higher.

Referring again the right portions of FIGS. 3(A) and 3(B), it can be observed that the relation between the measured voltages V1 and V2 are related to the distance between the locations 331 and 332 where those measurements are implemented. When the two locations 331 and 332 are either very close or far away, the difference between V1 and V2 is insignificant. While the two locations 331, 332 are right under the middle of the first and the second portions 321, 322 respectively, in other words the distance thereinbetween is about the half of the maximum distance the two locations 331, 332 could be disposed, a maximum difference of the two voltages V1 and V2 is obtained. Accordingly to a preferred embodiment, the two locations 331, 332 for data collecting are disposed near the center areas underneath the first and second portions 321, 322 of the measurement material 30, respectively.

Figure 4:
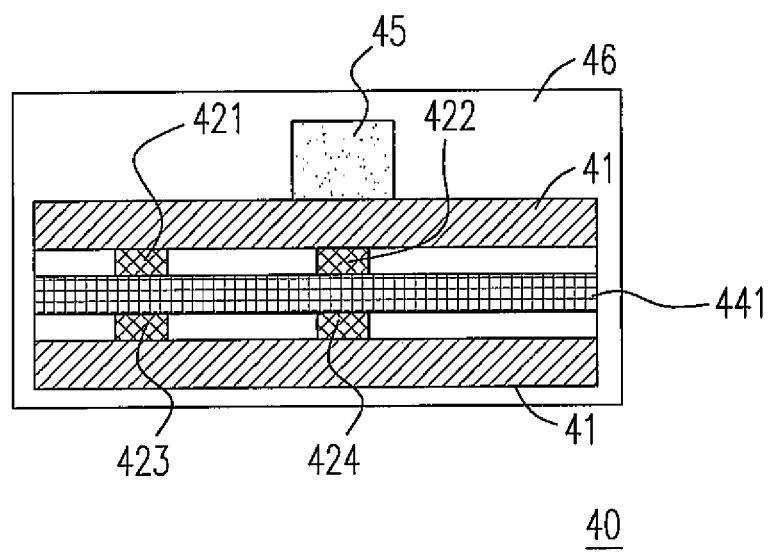
FIG. 4 is a schematic diagrams showing an apparatus for measuring a material property according to a preferred embodiment of the present invention.

Please refer to FIG. 4, which schematics the apparatus for measuring a material property according to a preferred embodiment of the present invention. According to FIG. 4, a pressure-sensing element 441 is attached with a first and a second electrodes 421, 422 on one side and a third and a fourth electrodes 423 and 424 on the other sides. Preferably, all those electrodes 421, 422, 423, and 424 are separately couple to two flexible substrates 41. The first electrode 421 and the second electrode 422 are separately disposed on the upper surface of the sensing element 441, and the third electrode 423 and the fourth electrode 424 are disposed on the lower surface of the sensing element 441 at locations corresponding to that of the first and second electrodes respectively, by properly arranging the position of the flexible substrates 41. Accordingly, the first and the third electrodes 421, 423 constitutes a pair of electrodes being able to transmit the voltage signal (not shown) due to pressure stress existing at the location of the sensing element 441 between the two electrodes 421 and 423 via the two flexible substrates.

Again, referring to FIG. 4, an elastic member 45 made of an elastic material such as emulsion, rubber, resin or silicone is disposed on top of the second electrode 422. The whole structure described above is packaged with a molding material 46, which has a mechanical property different from that of the elastic member 45, to form a measurement device 40.

It can be figured out by the skilled person in the art that, according to the illustration of FIG. 4, the elastic coefficient of the portion of the measurement device 40 above the first and the third electrodes 421, 423 must be different from that of the portion above the second and the third electrodes 422, 424, since the material property of the elastic member 45 differs from that of the molding material 46. Therefore, the measurement device 40 is applicable to be used according the abovementioned method for estimating a material property of a matter under test.

In the field of Mechanics of Materials, parameters commonly used for specifying mechanical properties include elastic coefficient, hardness, density and etc. The Young's Modulus (Modulus of Elasticity), which indicates a relation between tensile stress and elongation of a specimen, is a popular elastic coefficient. Commonly used hardness parameters include Rockwell and Shore hardness indicators, while the latter is applicable for soft materials such as rubber, resin, or emulsion who's hardness are close to that of the tissues of human's body.

Figure 5:
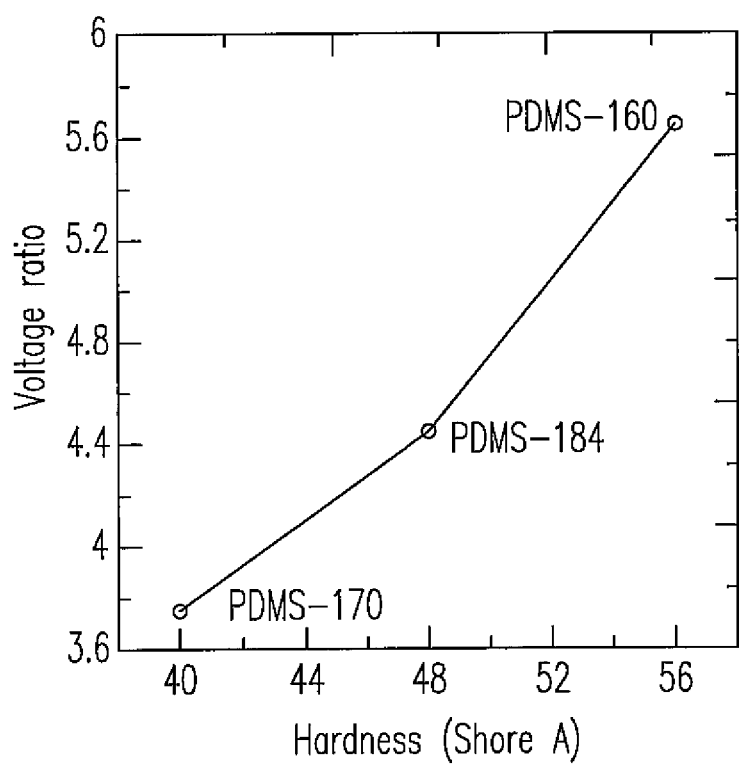
FIG. 5 is a schematic diagram showing an experiment result obtained by the method and measurement apparatus according to the present invention.

Please refer to FIG. 5, which schematics the relation of Shore's hardness of three test samples PDMS-170, PDMS184 and PDMS 160 (made by Dow-Corning Corp.) with the inspected voltage ratios by using the method according to the present invention. It can be observed that the data along the horizontal axis and those along the vertical axis are positively correlated. Therefore, one may estimate the Shore's hardness of an inspection matter contacted with the measurement device 40 based on the inspected voltage ratio. It is also observed that the differences of hardness among those samples are relatively small. All those test samples are soft materials whose hardness are close to that of the tissues of human beings or a living body (animal for example). Usually, an abnormal tissue (such as a tumor) inside a living body is tougher that a tissue under a normal health condition. Therefore, the present invention can be used to help medical experts to determine whether the inspected portion of a tissue includes a tumor or other abnormal tissues.

Figure 6:
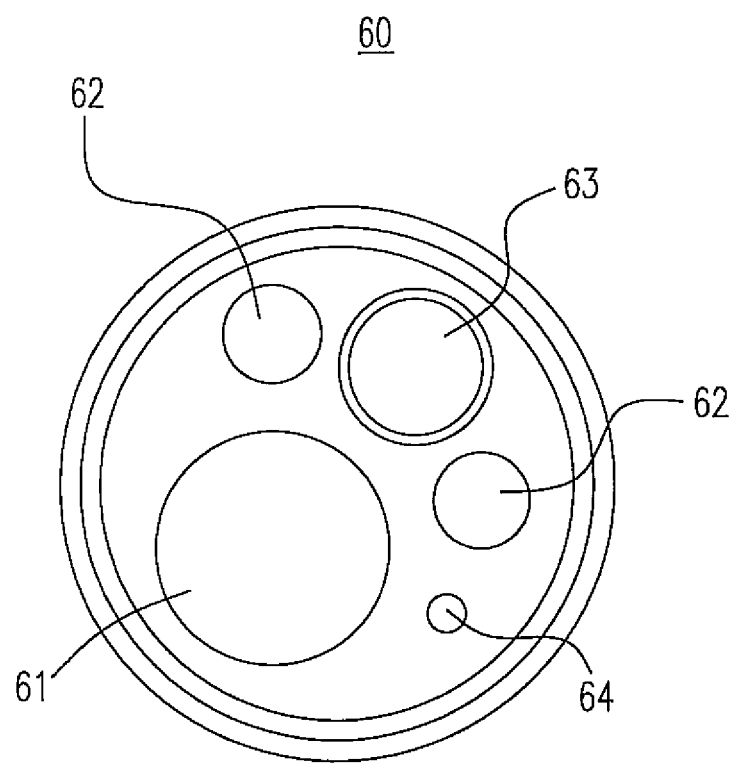
FIG. 6 is a cross-sectional diagram of a typical medical endoscope.

Please refer to FIG. 6, which illustrates a cross-sectional diagram of a typical medical endoscope. An endoscope 60 comprises an instrument channel 61, two light-transmission lens 62, an objective lens 63 and a water/gas nozzle 64. The present invention provides a simple method, which disposes a measurement device with the function of determining the toughness of a tissue (such as the measurement device 40) in the medical endoscope 60, to provide additional feedback related tactile information during endoscope operations. The diameter of the instrument channel 61 of a medical endoscope ranges from 1 to 6 millimeter. The present inventions provides a manipulating media with a configuration of tweezers, which is furnished with the measurement device on a surface of a grip of the manipulating media, and the measurement device is managed to get inside a human body for performing measurement or inspection. The way of measurement is mainly performed by griping a tissue for obtaining information regarding a material property thereof.

Figure 7A:
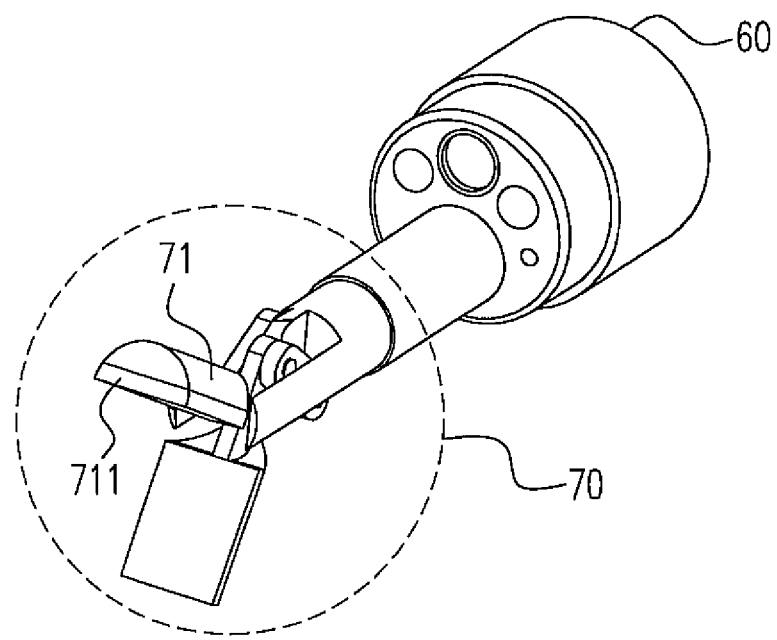
FIGS. 7(A) to 7(C) are schematic diagrams showing a manipulating device for handling sensing element in accordance with one preferred embodiment of the present invention.
Figure 7B:
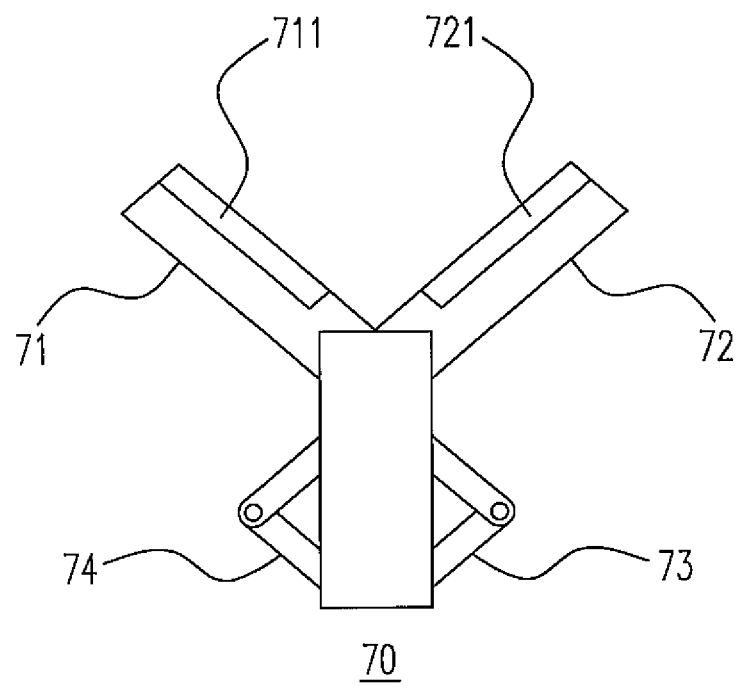
Figure 7C:
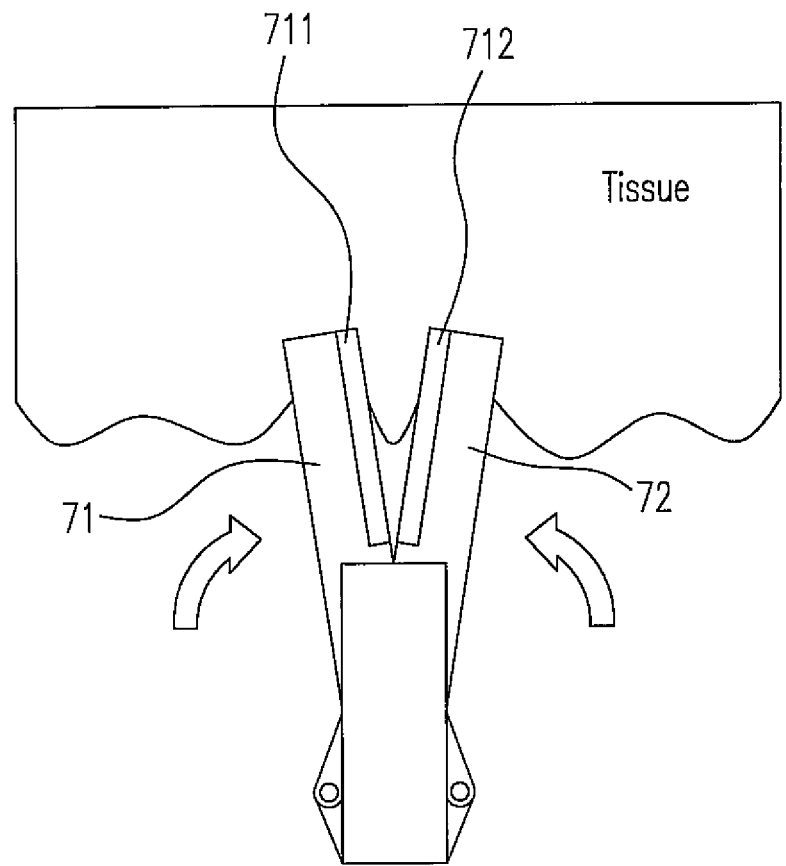
Figure 8:
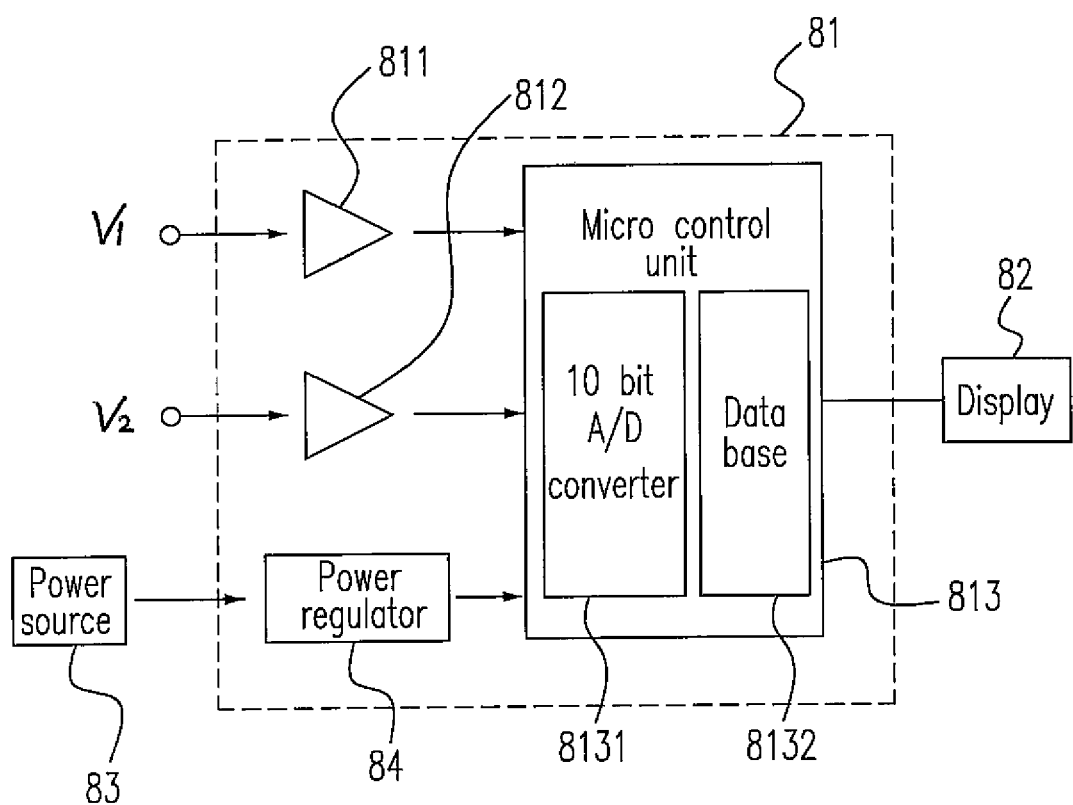
FIG. 8 illustrates an embodiment of an analyzing device according to the present invention.

Please refer to FIGS. 7(A) to 7(C), which schematic a manipulating device for handling sensing element according to a preferred embodiment of the present invention. In FIG. 7(A), a manipulating media 70 is disposed in the endoscope device 60, and capable for assisting all the original functions of the endoscope device 60, to enable a user to select a chosen area of a tissue for examination when observing the tissue inside a living body. The manipulating media 70 is equipped with a mechanism having a configuration of tweezers or a grip. It can be observed that a sensing element 711 is disposed on a linkage 71, and is able to measure parameters of tissues (such as elastic coefficient or hardness) inside a human body, under manipulations of the manipulating media 70. Information related to the parameters obtained by the sensing element 711 is analyzed by an analysis media (illustrated in FIG. 8 for example) to verify the meanings thereof. For example, comparing with known data records, one may determine whether the inspected tissue is a normal tissue or an ill one such as a tumor.

Referring to FIG. 7(B), the manipulating media 70 has a linkage structure, where a first linkage 71 and a second linkage 72 are furnished with sensing elements 711 and 712, respectively. Through the operational mechanism of linkage, a third linkage 73 and a fourth linkage 74 manipulate the movements of the first and the second linkages 71, 72, respectively.

FIG. 7 (C) shows the relative locations of the first and the second sensing elements 711, 712 respectively disposed on the linkages 71, 72, when the linkage mechanism is managed to grip a portion of a tissue. Both the sensing elements 711, 712 can be manipulated to contact the same portion of the tissue. Notable, the way of manipulating the first and the second linkages 71, 72 is not limited to the linkage structure shown in FIG. 7(B). The skilled person in the art is able to utilize a number of different methods to operate the first and the second linkages 71, 72. Besides, for the need of measuring a parameter (such as elastic coefficient or hardness) of a tissue inside a living body, either one of the mentioned sensing elements 711, 712 can be sufficiently used, according to the present embodiment. However, using the two sensing elements simultaneously can help in obtaining parameters from different locations of a tissue, which doubles the efficiency of inspection.

For the purpose of offering users the specialties of easy operating and instant identification of the target tissue under inspection, the present invention provides a modulized system for analyzing the meanings of the parameters mentioned above. Please refer to FIG. 8, which illustrates an embodiment of an analyzing device 81 utilizing distributed microelectronic elements to collect the output signals (a first set of voltage signals denoted with V1 and a second set of voltage signals denoted with V2) from an internal layer of the sensing element and an external packaging material thereof, respectively. When the sensing element contacts the inspected matter, the mentioned two sets of signals will be magnified by two amplifies 811, 812 respectively, transmitted into a micro control unit 813 for the calculation for estimating a material property based on voltage ratios. Voltage ratios and the corresponding values of parameters relevant to material properties has been previously stored in a data base 8132 of the micro control unit 813 for the need of cross referencing and estimating. Finally, the results (not shown) are outputted to a display 82. The material property related data corresponding to those voltage ratios shown in FIG. 5 are Shore hardness for example. The skilled person in the art may choose other parameters such as elastic coefficient or different hardness indicators for the use of determining the essence of the inspected matters based on calculated parameters.

According to the above, the present invention provides a method and apparatus being able to instantly verify the mechanical property of an inspected tissue inside a living body without the risk of massive hemorrhages during the operation for obtaining tissue slices inside the living body.

Embodiments:
1. An apparatus for performing a measurement inside a living body, comprising:
   a first sensing element performing the measurement;
   a manipulating device coupled to the first sensing element and manipulating the first sensing element; and
   an analyzing device for analyzing the measurement.
2. The apparatus of embodiment, wherein the first sensing element comprises:
   a pressure-sensing component having a first and a second surfaces;
   a first and a second electrodes separately disposed on the first surface;
   a third electrode disposed on the second surface and corresponding to the first electrode;
   a fourth electrode disposed on the second surface and corresponding to the second electrode; and
   an elastic member having a first and a second portions, and disposed on the first surface, wherein the first and the second portions of the elastic member have different values of an elastic coefficient, and cover the first and the second electrodes, respectively.
3. The apparatus of embodiment 2, further comprising a flexible substrate, and the first and the second electrodes are separately and electrically coupled to the flexible substrate.
4. The apparatus of embodiment 2, further comprising a flexible substrate, wherein the third and the fourth electrodes are separately and electrically coupled to the flexible substrate.
5. The apparatus of embodiment 2, wherein the elastic coefficient of the elastic member includes one selected from a group consisting of a Young's modules, a Rockwell hardness, a Brinell hardness and a Shore hardness.
6. The apparatus of embodiment 2, wherein the measurement is performed to obtain a physical property including one of an elasticity and a hardness.
7. The apparatus of embodiment 1, wherein the manipulating device manipulates the first sensing element to be contacted with a tissue of the living body, and comprises:
   an endoscope instrument tunnel; and
   a linkage mechanism disposed inside the endoscope instrument tunnel, wherein the linkage mechanism includes a first and a second linkages jointly connected, and the first sensing element is disposed on the first linkage.
8. The apparatus of embodiment 7, further comprising:
   a second sensing element disposed on the second linkage, and opposite to the first sensing element.
9. A sensing apparatus used inside a living body, comprising:
   a first tactile sensing element; and
   a manipulating device manipulating the first tactile sensing element.
10. The sensing apparatus of embodiment 9, wherein the first sensing element comprises:
    a pressure-sensing component having a first and a second surfaces;
    a first and a second electrodes separately disposed on the first surface;
    a third electrode disposed on the second surface and corresponding to the first electrode;
    a fourth electrode disposed on the second surface and corresponding to the second electrode; and
    an elastic member having a first and a second portions, and disposed on the first surface, wherein the first and the second portions of the elastic member have different values of an elastic coefficient, and cover the first and the second electrodes, respectively.
11. The sensing apparatus of embodiment 10, further comprising a flexible substrate, and the first and the second electrodes are separately and electrically coupled to the flexible substrate.
12. The sensing apparatus of embodiment 10, further comprising a flexible substrate, wherein the third and the fourth electrodes are separately and electrically coupled to the flexible substrate.
13. The sensing apparatus of embodiment 10, the elastic coefficient of the elastic member includes one selected from a group consisting of a Young's modules, a Rockwell hardness, a Brinell hardness and a Shore hardness.
14. The sensing apparatus of embodiment 9, wherein the manipulating device manipulates the first sensing element to be contacted with a tissue of the living body, and comprises:
    an endoscope instrument tunnel; and
    a linkage mechanism disposed inside the endoscope instrument tunnel, wherein the linkage mechanism includes a first and a second linkages jointly connected, and the first sensing element is disposed on the first linkage.
15. The sensing apparatus of embodiment 14, further comprising:
    a second sensing element disposed on the second linkage, and opposite to the first sensing element, wherein the linkage mechanism further comprises a third and a fourth linkages manipulating the first and the second linkages, respectively.
16. A method of measuring a tissue of a living body, comprising steps of:
    providing a pair of working elements pivotally connected;
    measuring a parameter of the tissue of the living body by using the pair of working elements; and
    analyzing the parameter.
17. The method of embodiment 16, wherein the parameter is relevant to a physical property including one of an elasticity and a hardness.
18. The method of embodiment 16, wherein the pair of working elements comprises:
    a tactile sensing component having a first and a second surfaces;
    a first and a second electrodes separately disposed on the first surface;
    a third electrode disposed on the second surface and corresponding to the first electrode;
    a fourth electrode disposed on the second surface and corresponding to the second electrode; and
    an elastic member having a first and a second portions, and disposed on the first surface, wherein the first and the second portions of the elastic member have different values of an elastic coefficient, and cover the first and the second electrodes, respectively.
19. The method of embodiment 18, wherein the elastic coefficient includes one selected from a group consisting of a Young's modulus, a Rockwell hardness, a Brinell hardness and a Shore hardness.
20. The method of embodiment 16, wherein the pair of working elements comprises a first and a second linkages, the first linkage is furnished with a tactile sensing element, and the method further comprises a step of contacting the tissue with the tactile sensing element to obtain the parameter by using the first and the second linkages.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims that are to be accorded with the broadest interpretation so as to encompass all such modifications and similar structures.

What is claimed is:

1. An apparatus for performing a measurement inside a living body, comprising:
    a first sensing element performing the measurement, wherein the first sensing element comprises:
        a pressure-sensing component having a first and a second surfaces;
        a first and a second electrodes separately disposed on the first surface;
        a third electrode disposed on the second surface and corresponding to the first electrode;
        a fourth electrode disposed on the second surface and corresponding to the second electrode; and
        an elastic member having a first and a second portions, and disposed on the first surface, wherein the first and the second portions of the elastic member have different elastic coefficients and cover the first and the second electrodes, respectively;
    a manipulating device coupled to the first sensing element and manipulating the first sensing element; and
    an analyzing device for analyzing the measurement.

2. An apparatus as claimed in claim 1, further comprising a flexible substrate, and the first and the second electrodes are separately and electrically coupled to the flexible substrate.

3. An apparatus as claimed in claim 1, further comprising a flexible substrate, wherein the third and the fourth electrodes are separately and electrically coupled to the flexible substrate.

4. An apparatus as claimed in claim 1, wherein the elastic coefficient of the elastic member includes one selected from a group consisting of a Young's modules, a Rockwell hardness, a Brinell hardness and a Shore hardness.

5. An apparatus as claimed in claim 1, wherein the measurement is performed to obtain a physical property including one of an elasticity and a hardness.

6. An apparatus as claimed in claim 1, wherein the manipulating device manipulates the first sensing element to be contacted with a tissue of the living body, and comprises:
    an endoscope instrument tunnel; and
    a linkage mechanism disposed inside the endoscope instrument tunnel, wherein the linkage mechanism includes a first and a second linkages jointly connected, and the first sensing element is disposed on the first linkage.

7. An apparatus as claimed in claim 6, further comprising:
    a second sensing element disposed on the second linkage, and opposite to the first sensing element.

8. A sensing apparatus used inside a living body, comprising:
    a first tactile sensing element, wherein the first tactile sensing element comprises:
        a pressure-sensing component having a first and a second surfaces:
        a first and a second electrodes separately disposed on the first surface;
        a third electrode disposed on the second surface and corresponding to the first electrode;
        a fourth electrode disposed on the second surface and corresponding to the second electrode: and
        an elastic member having a first and a second portions, and disposed on the first surface, wherein the first and the second portions of the elastic member have different elastic coefficients, and cover the first and the second electrodes, respectively; and
    a manipulating device manipulating the first tactile sensing element.

9. A sensing apparatus as claimed in claim 8, further comprising a flexible substrate, and the first and the second electrodes are separately and electrically coupled to the flexible substrate.

10. A sensing apparatus as claimed in claim 8, further comprising a flexible substrate, wherein the third and the fourth electrodes are separately and electrically coupled to the flexible substrate.

11. A sensing apparatus as claimed in claim 8, the elastic coefficient of the elastic member includes one selected from a group consisting of a Young's modules, a Rockwell hardness, a Brinell hardness and a Shore hardness.

12. A sensing apparatus as claimed in claim 8, wherein the manipulating device manipulates the first sensing element to be contacted with a tissue of the living body, and comprises:
    an endoscope instrument tunnel; and
    a linkage mechanism disposed inside the endoscope instrument tunnel, wherein the linkage mechanism includes a first and a second linkages jointly connected, and the first sensing element is disposed on the first linkage.

13. A sensing apparatus as claimed in claim 12, further comprising:
    a second sensing element disposed on the second linkage, and opposite to the first sensing element, wherein the linkage mechanism further comprises a third and a fourth linkages manipulating the first and the second linkages, respectively.

14. A method of measuring a tissue of a living body, comprising steps of:
    providing a pair of working elements pivotally connected, wherein the pair of working elements comprises:
        a tactile sensing component having a first and a second surfaces;
        a first and a second electrodes separately disposed on the first surface;
        a third electrode disposed on the second surface and corresponding to the first electrode;
        a fourth electrode disposed on the second surface and corresponding to the second electrode; and
        an elastic member having a first and a second portions, and disposed on the first surface, wherein the first and the second portions of the elastic member have different elastic coefficients, and cover the first and the second electrodes, respectively;
    measuring a parameter of the tissue of the living body by using the pair of working elements; and
    analyzing the parameter.

15. A method as claimed in claim 14, wherein the parameter is relevant to a physical property including one of an elasticity and a hardness.

16. A method as claimed in claim 14, wherein the elastic coefficient includes one selected from a group consisting of a Young's modulus, a Rockwell hardness, a Brinell hardness and a Shore hardness.

17. A method as claimed in claim 14, wherein the pair of working elements comprises a first and a second linkages, the first linkage is furnished with a tactile sensing element, and the method further comprises a step of contacting the tissue with the tactile sensing element to obtain the parameter by using the first and the second linkages.

* * * * *